United States Patent [19]
Bäbler

[11] Patent Number: 5,856,488
[45] Date of Patent: Jan. 5, 1999

[54] OXIDATION PROCESS FOR PREPARING QUINACRIDONE PIGMENTS

[75] Inventor: Fridolin Bäbler, Hockessin, Del.

[73] Assignee: Ciba Specialty Chemicals Corporation, Tarrytown, N.Y.

[21] Appl. No.: 854,235

[22] Filed: May 9, 1997

Related U.S. Application Data

[60] Provisional application No. 60/017,500 May 10, 1996.
[51] Int. Cl.⁶ .................................................. C07D 471/04
[52] U.S. Cl. ................................................................ 546/49
[58] Field of Search .................................................. 546/49

[56] References Cited

U.S. PATENT DOCUMENTS

| | | | |
|---|---|---|---|
| 3,475,436 | 10/1969 | Cooper et al. | 260/279 |
| 4,956,464 | 9/1990 | Bender et al. | 546/57 |
| 5,229,515 | 7/1993 | Pfenninger et al. | 546/49 |

FOREIGN PATENT DOCUMENTS

| | | |
|---|---|---|
| 0313965 | 5/1989 | European Pat. Off. . |
| 0517663 | 12/1992 | European Pat. Off. . |
| 1346126 | 11/1963 | France . |
| 1412911 | 8/1965 | France . |
| 1427311 | 12/1965 | France . |
| 1496960 | 8/1967 | France . |

OTHER PUBLICATIONS

Efimov, N.K. et al, Khim. Prom–st. (Moscow), 1995, 12, pp. 751–753, online abstract only.

*Primary Examiner*—Alan L. Rotman
*Assistant Examiner*—Charanjit S. Aulakh
*Attorney, Agent, or Firm*—Kevin T. Mansfield

[57] ABSTRACT

The present invention relates to a process of preparing quinacridone pigments in their specific crystal forms by oxidizing a premilled 6,13-dihydroquinacridone corresponding to the quinacridone pigment in a basic, aqueous reaction medium utilizing hydrogen peroxide as the oxidizing agent. The inventive process is an environmentally friendly process which yields a polymorphically homogeneous product in excellent yield.

31 Claims, No Drawings

OXIDATION PROCESS FOR PREPARING QUINACRIDONE PIGMENTS

This application claims the benefit under 35 U.S.C. 119(e) of U.S. Provisional Application No. 60/017,500, filed May 10, 1996.

SUMMARY

The present invention relates to a process for the preparation of quinacridone pigments by oxidation of the corresponding premilled 6,13-dihydroquinacridone in an aqueous, basic system using hydrogen peroxide as oxidant.

BACKGROUND

The oxidation of unsubstituted and substituted 6,13-dihydroquinacridone compounds to the corresponding quinacridone is well-known in the art.

For example, numerous publications disclose the oxidation of a 6,13-dihydroquinacridone to the corresponding quinacridone using aromatic nitro compounds as the oxidizing agent in an alcoholic medium containing a small amount of water. However, such processes have the disadvantage of producing considerable organic waste due to the generation of reduced aromatic by-products.

It is also known to oxidize a 6,13-dihydroquinacridone to the corresponding quinacridone by a process wherein the 6,13-dihydroquinacridone is oxidized in a solvent and/or aqueous basic system with an oxygen-containing gas. Such processes are often referred to as "air oxidation" because air is conveniently used as the oxygen containing-gas. Air oxidation processes have the disadvantage that large gas volumes have to be introduced into a heterogeneous reaction mixture, whereby foam is generated. Additionally, it is difficult to determine when the reaction is complete.

Furthermore it is known to oxidize 6,13-dihydroquinacridones dissolved in polar solvents, for example DMSO, using air as the oxidizing agent. Such processes have the advantage of generating excellent quinacridone pigments in a high yield. However, they have the disadvantage of producing a substantial amount of organic waste, such as dimethylsulfone, as by-product during the oxidation reaction, which requires costly solvent regeneration systems.

The present invention is based on the discovery that unsubstituted and substituted quinacridones are prepared by an environmentally friendly process whereby a premilled 6,13-dihydroquinacridone is oxidized to the corresponding quinacridone in an aqueous, basic medium using hydrogen peroxide as the oxidant. It is necessary to premill the 6,13-dihydroquinacridone in order to achieve an acceptable degree of oxidation when hydrogen peroxide is the oxidant.

The inventive process offers the advantage of oxidizing the 6,13-dihydroquinacridone without organic solvents and with only a small excess of base in an aqueous system. The hydrogen peroxide oxidant is additionally advantageous because it does not generate a reduced by-product, but rather oxidizes impurities present in the 6,13-dihydroquinacridone from the presynthesis steps. Thus, the inventive process produces a quinacridone product with improved purity and chroma. Additionally, less water has to be used to wash the presscake of the quinacridone product compared to the known oxidation processes.

In another related aspect, the present invention is based on the discovery that gamma-II quinacridone is obtained, if desired in polymorphically pure form, by an environmentally friendly process whereby finely milled 6,13-dihydroquinacridone is oxidized in a basic, aqueous medium using hydrogen peroxide as oxidant. Since the gamma-II form of quinacridone is widely used, the ability to produce it in polymorphically pure form by an anvironmentally friendly process is a great advantage.

DETAILED DESCRIPTION

The present invention relates to a process for preparing a quinacridone of the formula I

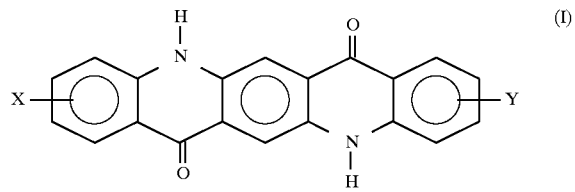

wherein X and Y are independently 1 or 2 substituents selected from the group consisting of H, F, Cl, $C_1$–$C_3$alkyl and $C_1$–$C_3$alkoxy, by the oxidation of a corresponding 6,13-dihydroquinacridone of the formula II

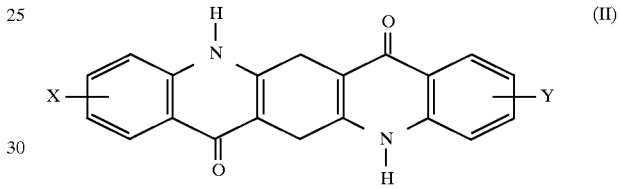

which comprises
  (a) premilling the 6,13-dihydroquinacridone of formula II to subpigmentary size;
  (b) oxidizing the premilled 6,13-dihydroquinacridone to the corresponding quinacridone in a basic, aqueous reaction medium with hydrogen peroxide in the presence of a catalyst; and
  (c) isolating the quinacridone of formula I.

During the premilling step, the particle size of the 6,13-dihydroquinacridone is reduced to subpigmentary size. In general, the subpigmentary, premilled 6,13-dihydroquinacridone is a highly aggregated, almost amorphous powder with very low crystallinity as can be demonstrated by x-ray diffraction. The premilling is controlled by assessing the width at half height of one of the main peaks in the x-ray diffraction pattern of the 6,13-dihydroquinacridone to be oxidized; the greater the width, the smaller the particle size of the premilled 6,13-dihydroquinacridone powder.

Premilling as used in this application, in particular, includes milling in the complete absence of liquids. However, it is possible for a liquid, such as a phase directing or a surface active agent, to be present in small amounts, usually up to a maximum of about 10% by weight, based on the weight of the milling composition, which includes the 6,13-dihydroquinacridone and inorganic salts used as milling aids. The 6,13-dihydroquinacridone should retain the characteristics of a powder.

Premilling operations are known and can be accomplished in various ways. Thus, it is possible to premill with steel balls and roofing nails, or, in order to avoid metal attrition and the corresponding need for 6,13-dihydroquinacridone extraction with dilute acid, premilling can be accomplished with stainless steel balls, rods or ceramic beads made, for example, from crystalline zirconia phase and amorphous silica phase by fusion of the oxides. Stainless steel or ceramic beads of 0.5 to 2.5 cm size are particularly suitable. Although a variety of sizes of grinding medium can be used, the aforementioned sizes are preferred.

Many suitable grinding apparatus are also known. Examples of such suitable apparatus include a ball mill, or an attritor mill filled with metal or porcelain balls, or preferably with stainless steel or ceramic beads.

A preferred means of accomplishing the premilling step is to premill the 6,13-dihydroquinacridone in an attritor mill, in the absence of a salt, under an inert atmosphere, such as nitrogen (to prevent explosions), using stainless steel or ceramic beads as grinding medium.

In an alternate embodiment, the 6,13-dihydroquinacridone is premilled in the presence of 10–30% of an inorganic salt, such as, NaCl, $CaCl_2$, $Na_2SO_4$ or $Al_2(SO_4)_3$, with or without water of hydration. A preferred milling mixture composition is composed of from about. 75 to 85% 6,13-dihydroquinacridone and from about 15 to 25% of anhydrous $Na_2SO_4$. The salt is primarily present to suppress the potential explosive nature of the resulting millpowder.

The premilled 6,13-dihydroquinacridone is separated from the grinding medium by sieving or another suitable method. The premilled 6,13-dihydroquinacridone is then ready for the oxidation reaction.

The premilled 6,13-dihydroquinacridone is easily oxidized in an aqueous basic medium in the presence of a catalyst, such as an anthraquinone derivative, with an aqueous solution of hydrogen peroxide at a temperature above 60° C., preferably in the range from about 80° to about 103° C., and most preferably in the range from 90° to 100° C.

Since 6,13-dihydroquinacridone that has not been premilled is only partially oxidized under the same conditions, the usefulness of the inventive process to prepare quinacridone and quinacridone solid solution pigments in acceptable yields is unexpected.

According to the inventive process, the yield of the quinacridone product based on the 6,13-dihydroquinacridone is above about 80 percent of theory. For certain quinacridone products, for example unsubstituted quinacridone, the yield is generally in the range from 90 to 99.8 percent of theory. In general, the resulting quinacridone is polymorphically homogeneous, meaning that the x-ray diffraction pattern of the quinacridone product displays substantially the pattern of only one crystalline polymorph, but normally contains some 6,13-dihydroquinacridone which is not oxidized, so that the mass yield is normally close to 100 percent.

According to the present process, the oxidation of the 6,13-dihydroquinacridone to the corresponding quinacridone is carried out in a basic, aqueous medium which is a slurry consisting essentially of the premilled 6,13-dihydroquinacridone, water, base, catalyst and oxidizing agent or the premilled 6,13-dihydroquinacridone, water, base, catalyst, oxidizing agent and an antifoam agent.

In general, the basic, aqueous reaction medium contains an amount of water equal to from about 2 to 20 times, preferably 3 to 14 times, the weight of the 6,13-dihydroquinacridone.

In a preferred embodiment of this invention, the basic, aqueous reaction medium is substantially free of organic solvents other than an antifoam agent. However, organic solvents are tolerated in the basic, aqueous reaction medium as long as they do not impair the generation of the corresponding quinacridone or quinacridone solid solution in its desired crystal modification.

Suitable bases include the alkali metal hydroxides, such as sodium hydroxide or, preferably, potassium hydroxide. In general, the basic aqueous reaction medium contains from 2 to 7 moles of base per mole of the 6,13-dihydroquinacridone. Preferably, the basic, aqueous reaction medium contains 2.2 to 5 moles of base per mole of the 6,13-dihydroquinacridone.

Preferably, step (b) is carried out by combining an aqueous solution of the oxidant hydrogen peroxide with a basic, aqueous slurry of the 6,13-dihydroquinacridone over a period of time at a temperature above 60° C., preferably above 80° C., in particular in the range from 80° to 103° C., and most preferably in the range from 90° to 100° C. The aqueous solution of hydrogen peroxide generally contains from 1 to 50 weight percent, preferably 5 to 30 weight percent, and most preferably 10 to 25 weight percent, of hydrogen peroxide.

In general, an excess of the hydrogen peroxide is used, for example, from 1.1 to 5 moles, preferably 1.2 to 3 moles, of hydrogen peroxide per mole of the 6,13-dihydroquinacridone.

The presence of the catalyst during the oxidation step leads to a higher yield of quinacridone. Additionally, the presence of the catalyst at the oxidation conditions described above, results in a quinacridone product that is substantially free of quinacridonequinone, for example containing less than 2.5 percent by weight of quinacridonequinone. However, minor amounts of quinacridonequinone are tolerated in the product as long as its presence does not substantially reduce the saturation of the final quinacridone pigment.

Particularly suitable catalysts used in the inventive process are, for example, the quinone compounds used for the air oxidation of 6,13-dihydroquinacridone to quinacridone. Such quinone catalysts are well-known in the art. In particular, suitable catalysts include anthraquinone compounds, especially anthraquinone, and anthraquinone sulfonic acid derivatives, such as anthraquinone-2,6-disulfonic acid or preferably anthraquinone-2-sulfonic acid, or salts thereof, in particular the sodium or potassium salts, especially anthraquinone-2-sulfonic acid, sodium or potassium salt. The quinone catalyst is present in the basic, aqueous reaction medium in an amount ranging from 0.005 to 0.1 times the weight of 6,13-dihydroquinacridone, and most preferably 0.01 to 0.05 times the weight of 6,13-dihydroquinacridone.

Without limiting this invention to any particular theory, it is believed that the quinone catalyst acts to oxidize the 6,13-dihydroquinacridone and is itself reduced to the corresponding leuco compound, which is then regenerated by the hydrogen peroxide.

The catalyst is added according to this invention before, during or after the premilling step. For example, the catalyst is added simultaneously with the 6,13-dihydroquinacridone by feeding an attritor mill with both followed by premilling the resulting mixture.

To avoid the generation of foam during the addition of hydrogen peroxide, the presence of a small amount of an antifoam agent is usually advantageous, as long as the desired crystal phase of the quinacridone pigment is generated. Preferably the antifoam agent is used in an amount of from 0.1 to 6 percent by weight based on the 6,13-dihydroquinacridone, preferably from 0.5 to 4 percent.

Suitable antifoam agents are, for example, $C_5$–$C_{12}$alkyl alcohols such as iso-octanol, alkylenediols such as 1,2-hexanediol or 1,2-dodecanediol; polyalkylene glycol or polyalkylene glycol derivatives such as for example cetyloxypoly(ethylenoxy)ethanol with an average molecular weight of around 620; alkylphenoxypoly(ethyleneoxy) ethanol; or tertiary ammonium compounds such as benzyltributyl ammonium chloride. Many suitable antifoam agents are available commercially.

In an optimized process according to this invention, step (b) is carried out by combining an aqueous solution of hydrogen peroxide with the aqueous slurry of the premilled 6,13-dihydroquinacridone over a time interval of from ½ to 9 hours, preferably over 1 to 8 hours, and stirring the aqueous, basic reaction medium at an elevated temperature for a period of time to complete the oxidation and promote pigment recrystallization. Preferably, the basic, aqueous reaction medium is stirred at a temperature of from 90° to 100° C. for ½ to 12 hours, preferably 1 to 6 hours, after the addition of the hydrogen peroxide. The pigment is then isolated by filtration, washed with hot water and dried.

Depending on the recrystallization time and temperature, transparent smaller particle size or opaque larger particle size quinacridone pigments are generated. Lower temperatures and shorter times favor a transparent product, while higher temperatures and longer times favor a more opaque product.

Additionally it can be advantageous to add particle growth inhibitors to control the pigment particle size of the oxidized quinacridone pigment. Particle growth inhibitors, also known as antiflocking agents, are well known. Suitable particle growth inhibitors include, for example, phthalimidomethylquinacridone, quinacridone sulfonic acid and its salts, for example the aluminum salt, and pyrazolylmethylquinacridone.

The instant process is especially useful for the preparation of quinacridone, 2,9-dichloroquinacridone, 2,9-difluoroquinacridone, 4,11-dichloroquinacridone, 2,9-dimethylquinacridone and 2,9-dimethoxyquinacridone.

Additionally, the process is also suitable for the preparation of solid solutions containing one or more quinacridone components. Thus, an aspect of this invention relates to the process wherein the premilled 6,13-dihydroquinacridone is a mixture containing two or more 6,13-dihydroquinacridones of formula II which are co-oxidized by the process described in step (b) above to yield a quinacridone which is a solid solution.

The process of this invention is particularly practical for the preparation of quinacridone/2,9-dichloroquinacridone, quinacridone12,9-dimethylquinacridone, quinacridone/quinacridonequinone, 2,9-dichloroquinacridone/2,9-dimethylquinacridone or 2,9-dichloroquinacridone/2,9-dimethoxyquinacridone solid solution pigments.

The quinacridone product of the inventive process generally contains some unreacted 6,13-dihydroquinacridone, which is incorporated in the quinacridone pigment or solid solution crystal lattice. Preferably, the quinacridone product contains less than 15% of the 6,13-dihydroquinacridone by weight, most preferably the amount of the 6,13-dihydroquinacridone incorporated into the quinacridone product is limited to an amount in the range of from 1 to 10% by weight.

The process of this invention is particularly suitable for the preparation of specific crystal modifications of the unsubstituted or substituted quinacridones, for example, the alpha, beta or gamma form of the unsubstituted quinacridone, the beta form of 2,9-dimethylquinacridone and the alpha form of 2,9-dichloroquinacridone.

Different crystal forms of the quinacridone product are generated depending the reaction conditions used, such as, for example, the kind and concentration of base, the substantial pigmentary state of the premill powder which is characterized by the crystallinity of the premilled powder and/or the kind and concentration of the above mentioned antifoam and/or antiflocculating agents which may be present during the oxidation step.

The inventive process is particularly suitable for the preparation of the gamma-II crystal modification of the unsubstituted quinacridone described in U.S. Pat. No. 2,844,581. The gamma-II form of quinacridone is characterized by an x-ray diffraction pattern with three strong lines at 6.6, 13.9 and 26.3; five medium lines at 13.2, 13.4, 23.6, 25.2 and 28.3; and two weak lines at 17.1 and 20.4 degrees 2θ double glancing angles.

The gamma-II quinacridone prepared according to the inventive process is preferably polymorphically homogeneous, meaning that the product is substantially free of other crystalline forms of unsubstituted quinacridone.

When the product of the inventive process is gamma-II quinacridone, it also generally contains some unreacted 6,13-dihydroquinacridone, which is incorporated in the gamma-II quinacridone pigment crystals. In general, the gamma-II quinacridone pigment crystals incorporate up to about 15 percent by weight of 6,13-dihydroquinacridone in the form of a pigment solid solution having an x-ray diffraction pattern with peaks corresponding to those of gamma-II quinacridone. However, the location of the peaks may be shifted somewhat. Such solid solutions have been described in the literature as solid compounds.

Thus, the present process includes the process wherein the resulting gamma-II quinacridone product is a solid solution which displays the x-ray diffraction pattern of gamma-II quinacridone, in particular solid solutions which consist of quinacridone and 6,13-dihydroquinacridone. In general, the solid solution products prepared according to the inventive process contain from about 85 to 99.8 percent, preferably 90 to 99.5 percent and most preferably 92 to 99 percent by weight, of quinacridone, based on the combined weights of the quinacridone and 6,13-dihydroquinacridone, and 0.2 to 15 percent, preferably 0.5 to 10 percent, and most preferably 1 to 8 percent by weight of 6,13-dihydroquinacridone. Thus, the present invention relates to the process wherein the gamma-II quinacridone is in the form of a solid solution wherein the pigment solid solution has an x-ray diffraction pattern characterized by strong lines 6.6±0.2, 13.9±0.2 and 26.3±0.2; medium lines at 13.3±0.2, 23.6±0.2, 25.2±0.2 and 28.3±0.2; and weak lines at 17.1±0.2 and 20.4±0.2 degree 2θ double glancing angles, whereby the peak at 13.3 2θ double glancing angle consists of the two overlapped 13.2 and 13.4 degrees 2θ double glancing angle peaks.

Depending on the end use, it can be advantageous to add texture improving agents before the filtration of the pigment, preferably by blending into the aqueous presscake. Suitable texture improving agents are, in particular, fatty acids of not less than 18 carbon atoms, for example stearic or behenic acid or the amides or metal salts thereof, preferably calcium or magnesium salts, as well as plasticizers, waxes, resin acids such as abietic acid or metal salts thereof, colophonium, alkyl phenols or aliphatic alcohols such as stearyl alcohol or vicinal diols such as dodecanediol-1,2, and also modified colophonium/maleate resins or fumaric acid/colophonium resins or polymeric dispersants. The texture improving agents are preferably added in amounts of 0.1 to 30% by weight, most preferably of 2 to 15% by weight, based on the final product.

The present quinacridone and quinacridone solid solution pigments are highly suitable for coloring high molecular weight materials, which can be processed to cast and molded articles or which are used in ink and coating compositions such as solvent or water-based coatings.

Suitable high molecular weight organic materials include thermoplastics, thermoset plastics or elastomers, for example, cellulose ethers; cellulose esters such as ethyl cellulose; linear or crosslinked polyurethanes; linear, crosslinked or unsaturated polyesters; polycarbonates, polyolefins such as polyethylene, polypropylene, polybutylene or poly-4-methylpent-1-ene; polystyrene; polysulfones; polyamides, polycycloamides, polyimides, polyethers, polyether ketones such as polyphenylene oxides, and also poly-p-xylene, polyvinyl halides such as polyvinyl chloride, polyvinylidene chloride, polyvinylidene fluoride or polytetrafluoroethylene, acrylic polymers such as polyacrylates, polymethacrylates or polyacrylonitrile, rubber, silicone polymers, phenol/formaldehyde resins, melamine/formaldehyde resins, urea/formaldehyde resins, epoxy resins, styrene butadiene rubber, acrylonitrile-butadiene rubber or chloroprene rubber, singly or in mixtures.

Generally, the pigments are used in an amount of 0.01 to 30% by weight, preferably 0.1 to 10% by weight, based on the weight of the high molecular weight organic material to be pigmented. Thus, the present invention also relates to a pigmented plastic composition which comprises a plastic material and from 0.01 to about 30 percent by weight, based on the weight of said pigmented plastic composition, of a pigment or pigment solid solution prepared according to a process of the present invention, and to a process for preparing said pigmented plastic compositions.

The present pigments are highly dispersible and can be readily incorporated into organic matrixes to provide homogenous colorations possessing high saturation and excellent light and weather fastness properties.

The high molecular weight organic materials are pigmented with the pigments of the present invention by mixing the pigments, if desired in the form of a masterbatch, into substrates using high shear techniques including roll mills or a mixing or grinding apparatus. The pigmented material is then brought into the desired final form by known methods, such as calandering, pressing, extruding, brushing, casting or injection molding. The pigmented molded articles utilizing the present compositions are, in particular, those obtained by orienting stress, for example, molding and casting, ribbons, fibers or rolled sheets.

The following examples further describe embodiments of this invention. In these examples all parts given are by weight unless otherwise indicated. The x-ray diffraction patterns are measured on a RIGAKU GEIGERFLEX diffractometer type D/MaxII v BX.

EXAMPLE 1A

A model 1-SDG attritor mill manufactured by Union Process, Inc., Akron, Ohio, is charged with 485 grams 6,13-dihydroquinacridone and 15 grams anthraquinone-2-sulfonic acid sodium salt. The mill is fitted with L-arms and charged with 3.78 liters of 0.6 cm diameter stainless steel beads as grinding medium. The mill is then rotated at 500 rpm under nitrogen for 70 minutes. At the conclusion of the milling cycle, the premilled mixture is recovered by opening the valve at the bottom of the mill while rotation continues for 15 minutes, to yield 465 grams highly aggregated reddish premill powder.

As is known for a person skilled in the art, the yield of a single run in an attritor is not representative due to some product build up on the milling media. Preferably the attritor is run continuously in a production unit.

The x-ray diffraction pattern of the premill powder shows a width at half height at the 6.3° 2θ double glancing angle band of 0.9° 2θ whereas the width at half height at the 6.3° 2θ double glancing angle band of the starting material is 0.3° 2θ.

EXAMPLE 1B

60 Grams of the premilled mixture prepared in Example 1A, 100 ml water and 2.4 grams antifoam agent which is an oxyalkylated alkyl alcohol (FLO MO AJ-100 from WITCO Corp.) are added to a 1 liter flask equipped with stirrer, condenser, thermometer and a dropping funnel. The mixture is stirred until the premilled powder is completely wetted. 71.7 grams of 45% aqueous potassium hydroxide solution, followed by 70 ml water are added. The suspension is heated to 90° C. with stirring. Then 56 ml of a 16.2% aqueous hydrogen peroxide solution are slowly added via dropping funnel over a time interval of 7 hours at 95° to 100° C. The reaction mixture becomes thicker as a function of the reaction time and has to be diluted periodically with about 150 ml of water in total. The resulting red pigment suspension is further stirred at 95°–100° C. for ½ hour; then filtered. The presscake is washed with hot water to a pH of 8.0 and dried.

The red quinacridone pigment shows the x-ray diffraction pattern of a gamma-II quinacridone, characterized by the following data:

| scattering angle °2θ | relative intensity % |
|---|---|
| 6.64 | 100 |
| 13.35 (overlapped) | 59 |
| 13.98 | 73 |
| 17.25 | 12 |
| 20.42 | 15 |
| 23.66 | 15 |
| 25.25 | 23 |
| 26.31 | 65 |
| 28.35 | 21 |

An analytical evaluation of the red quinacridone pigment by spectrophotometric method shows a quinacridone-quinone content of less than 1.5% and a 6,13-dihydroquinacridone content of 5.9%.

By rubout according to ASTM method D-387-60 in a lithographic varnish, the pigment shows an opaque bluish-red masstone and a strong red color in $TiO_2$ extension. When incorporated into plastics or paints, the pigment imparts a bluish-red color with excellent fastness properties.

EXAMPLE 2A

The procedure of Example 1A was repeated utilizing 485 grams of 2,9-dimethyl-6,13-dihydroquinacridone instead of 6,13-dihydroquinacridone yielding 465 grams of premilled 2,9-dimethyl-6,13-dihydroquinacridone/anthraquinone-2-sulfonic acid sodium salt mixture.

The x-ray diffraction pattern of the premill powder shows a width at half height at the 26° 2θ double glancing angle band of 1.36° 2θ whereas the width at half height at the 26° 2θ double glancing angle band of the starting material is in the range of 0.5° 2θ.

EXAMPLE 2B

40 Grams of the premilled mixture prepared in Example 2A, 100 ml water and 1.6 grams of an antifoam agent which is an oxyalkylated alkyl alcohol (FLO MO AJ-100 from WITCO Corp.) are added to a 1 liter flask equipped with stirrer, condenser, thermometer and a dropping funnel. The mixture is stirred until the premilled powder is completely wetted. 43.7 grams of 45% aqueous potassium hydroxide solution are added. The suspension is heated to 94° C. with stirring. 31 ml of a 20.3% aqueous hydrogen peroxide solution are slowly added via dropping funnel over a time interval of 4 hours at 95° to 100° C. The resulting magenta pigment suspension is further stirred at 95°–100° C. for 6 hours, then filtered. The presscake is washed with hot water to a pH of 8.0 and dried.

The resulting magenta 2,9-dimethylquinacridone pigment shows the x-ray diffraction pattern of a beta 2,9-dimethylquinacridone, characterized by the following data:

| scattering angle °2θ | relative intensity % |
|---|---|
| 5.46 | 100 |
| 11.1 | 25 |
| 13.91 | 65 |
| 15.29 | 17 |
| 18.41 | 10 |
| 22.52 | 18 |
| 23.69 | 19 |
| 25.34 | 43 |
| 27.12 | 81 |
| 28.19 | 17 |

By rubout according to ASTM method D-387-60 in a lithographic varnish, the pigment shows a strongly magenta colored masstone. When incorporated into plastics or paints, the pigment imparts a bluish-red color with excellent fastness properties.

EXAMPLE 3A

The procedure of Example 1A was repeated utilizing 485 grams of 2,9-dichloro-6,13-dihydroquinacridone instead of 6,13-dihydroquinacridone and the mill was run for 30 minutes instead of 70 minutes to yield 462 grams of premilled 2,9-dichloro-6,13-dihydroquinacridone/anthraquinone-2-sulfonic acid sodium salt mixture.

The x-ray diffraction pattern of the premill powder shows a width at half height at the 26.6° 2θ double glancing angle band of 2.3° 2θ whereas the width at half height at the 26.6° 2θ double glancing angle band of the starting material is around 0.5° 2θ.

EXAMPLE 3B

40 Grams of the premilled mixture prepared in Example 3A, 100 ml water and 1.6 grams of an antifoam agent, 1,2-dodecanediol, are added to a 1 liter flask equipped with stirrer, condenser, thermometer and a dropping funnel. The mixture is stirred until the premilled powder is completely wetted. Then 49.0 grams of 45% aqueous potassium hydroxide solution are added. The suspension is heated to 94° C. with stirring. 35 ml of a 20% aqueous hydrogen peroxide solution are slowly added via dropping funnel over a time interval of 4 hours at 95° to 100° C. The resulting magenta pigment suspension is further stirred at 95° to 100° C. for 6 hours, then filtered. The presscake is washed with hot water to a pH of 8.0 and dried.

The product shows the X-ray diffraction pattern of a 2,9-dichloroquinacridone mainly in its alpha crystal form. By rubout according to ASTM method D-387-60 in a lithographic varnish, the pigment shows a magenta colored masstone.

EXAMPLE 4A

A model 1-SDG attritor mill manufactured by Union Process, Inc., Akron, Okla. is charged with 300 grams 6,13-dihydroquinacridone, 200 grams 2,9-dichloro-6,13-dihydroquinacridone and 15 grams anthraquinone-2-sulfonic acid sodium salt. The mill is fitted with L-arms and charged with 3.78 liters of 0.6 cm diameter stainless steel beads grinding medium. The mill is then rotated at 500 rpm under nitrogen for 60 minutes. At the conclusion of the milling cycle, the premilled mixture is recovered by opening the valve at the bottom of the mill while rotation continues for 15 minutes, yielding 457 grams highly aggregated reddish premill powder.

The x-ray diffraction pattern of the premill powder shows a width at half height at the 26° 2θ double glancing angle band of 2.75° 2θ.

EXAMPLE 4B

40 Grams of the premilled mixture prepared in Example 4A, 70 ml water and 1.2 grams antifoam agent, 1,2-dodecanediol, are added to a 1 liter flask equipped with stirrer, condenser, thermometer and a dropping funnel. The mixture is stirred until the premilled powder is completely wetted. Then 87.4 grams of 45% aqueous potassium hydroxide solution are added. The suspension is heated to 94° C. with stirring. 37.1 grams of a 16.1% aqueous hydrogen peroxide solution are slowly added via dropping funnel over a time interval of 4 hours at 95° to 100° C. The resulting red pigment suspension is further stirred at 95°–100° C. for 6 hours, then filtered. The presscake is washed with hot water to a pH of 8.0 and dried.

The red pigment powder shows the x-ray diffraction pattern of a solid solution pigment characterized by the following data:

| scattering angle °2θ | relative intensity % |
|---|---|
| 6.02 | 100 |
| 12.04 | 26 |
| 13.72 | 86 |
| 14.81 | 34 |
| 18.19 | 17 |
| 22.45 | 23 |
| 24.82 | 38 |
| 26.84 | 64 |
| 27.64 | 67 |

By rubout according to ASTM method D-387-60 in a lithographic varnish, the pigment shows a strongly red colored masstone.

EXAMPLE 5A

The procedure of Example 1A is repeated running the attritor mill for 30 minutes instead of 70 minutes to yield 460 grams of premilled 6,13-dihydroquinacridone/anthraquinone-2-sulfonic acid sodium salt mixture.

The x-ray diffraction pattern of the premill powder shows a width at half height at the 6.3° 2θ double glancing angle band of 0.7° 2θ whereas the width at half height at the 6.3° 2θ double glancing angle band of the starting material is 0.3° 2θ.

EXAMPLE 5B

40 Grams of the premilled mixture prepared in Example 5A, 100 ml water and 0.8 grams antifoam agent which is an oxyalkylated alkyl alcohol (FLO MO AJ-100 from WITCO Corp.) are added to a 1 liter flask equipped with stirrer, condenser, thermometer and a dropping funnel. The mixture is stirred until the premilled powder is completely wetted. Then 30.7 grams of 50% aqueous sodium hydroxide solution, followed by 30 ml water, are added. The suspension is heated to 90° C. with stirring. 56 ml of a 16.2% aqueous hydrogen peroxide solution are slowly added via dropping funnel over a time interval of 3 hours at 95° to 100° C. The reaction mixture becomes thicker as a function of the reaction time and has to be diluted periodically with about 100 ml water in total. The resulting red pigment suspension is further stirred at 95°–100° C. for 4½ hours, then filtered. The presscake is washed with hot water to a pH of 8.0 and dried.

The red quinacridone pigment shows the x-ray diffraction pattern of an alpha quinacridone, characterized by the following data:

| scattering angle °2θ | relative intensity % |
|---|---|
| 6.22 | 100 |
| 12.44 | 31 |
| 13.87 | 43 |
| 21.75 | 5 |
| 25.05 | 11.9 |
| 26.57 | 10 |
| 27.8 | 12 |

By rubout according to ASTM method D-387-60 in a lithographic varnish, the pigment shows a strongly red colored masstone.

EXAMPLE 6

The procedure of Example of 5B is repeated utilizing 1,2-dodecanediol as an antifoam agent, instead of an oxyalkylated alkyl alcohol, and adding the aqueous hydrogen peroxide solution over a time interval of 4 hours instead of 3 hours, and stirring the reaction mixture for 9 hours to yield a bluish-red pigment which shows the x-ray diffraction pattern of a beta quinacridone in mixture with a small amount of alpha quinacridone. By rubout according to ASTM method D-387-60 in a lithographic varnish, the pigment shows a bluish-red colored masstone and violet color in $TiO_2$ extension.

EXAMPLE 7

This Example illustrates the incorporation of the gamma-II quinacridone prepared according to Example 1 into an automotive paint system.
millbase formulation
A pint jar is charged with 66 grams acrylic resin, 14.5 grams AB dispersant and 58.1 grams solvent (SOLVESSO 100 from American Chemical). 26.4 grams gamma-II quinacridone obtained according to Example 1B and 980 grams of 4 mm diameter steel diagonal rods are added. The mixture is milled in the jar for 64 hours on a roller mill. The millbase contains 16.0% pigment with a pigment/binder ratio of 0.5 and a total nonvolatile content of 48.0%.

EXAMPLE 7A

Masstone Color 47.3 Grams of the above millbase, 36.4 grams of clear solids color solution containing a melamine resin catalyst, nonaqueous dispersion resin and a UV absorber, and 16.3 grams of a balanced clear solid color solution containing a polyester urethane resin are mixed and diluted with a solvent mixture containing 76 parts xylene, 21 parts butanol and 3 parts methanol to a spray viscosity of 20–22 seconds measured by a #2 Fisher Cup.

The red resin/pigment dispersion is sprayed onto a panel twice in a 1.5 minute interval as basecoat. After 2 minutes, clearcoat resin is sprayed twice at 1½ minute intervals onto the basecoat. The sprayed panel is then flashed with air in a flash cabinet for 10 minutes and then "baked" in an oven at 265° F. (129° C.) for 30 minutes, yielding a high chroma red colored panel, with excellent weatherability.

EXAMPLE 7B

Tint Color
white base
A $TiO_2$ dispersion is prepared by mixing the following ingredients in a quart glass jar:
604.1 grams of a $TiO_2$ pigment,
129.8 grams of acrylourethane resin, and
161.1 grams of solvent (SOLVESSO 100).
1 pint of ½" ceramic balls are then added. The dispersion is then milled for 24 hours. The white pigment dispersion is separated from the balls yielding a "TiO2 dispersion" containing 67.5% pigment with a total solid content of 77.4% solids.

A 10/90 tint shade is prepared by mixing the following ingredients: 15.7 grams mill base, 33.4 grams white base, 20.0 grams of clear solids color solution containing a melamine resin catalyst, nonaqueous dispersion resin and a UV absorber, and 30.9 grams of a clear solids color solution containing a polyester urethane resin. The paint contains 25.1% pigment with a pigment/binder ratio of 0.7 and a total non volatile content of 60.9%.

The red pigment/$TiO_2$/resin dispersion is sprayed onto a panel followed by a clearcoat as described in Example 5A, yielding a high gloss red tinted panel with excellent weatherability.

EXAMPLE 8

63.0 Grams of polyvinylchloride, 3.0 grams epoxidized soya bean oil, 2.0 grams of barium/cadmium heat stabilizer, 32.0 grams dioctyl phthalate and 1.0 gram of the pigment composition prepared according to Example 1 are mixed together in a glass beaker using a stirring rod. The mixture is formed into a soft PVC sheet with a thickness of about 0.4 mm by rolling for 8 minutes on a two roll laboratory mill at a temperature of 160° C., a roller speed of 25 rpm and friction of 1:1.2 by constant folding, removal and feeding. The resulting soft PVC sheet is colored in an attractive red shade with excellent fastness to heat, light and migration.

EXAMPLE 9

5 Grams of the pigment composition prepared according to Example 1, 2.5 grams hindered amine light stabilizer, 1.0 gram benzotriazole UV absorber, 1.0 gram hindered phenol antioxidant and 1.0 gram phosphite process stabilizer are mixed together with 1000 grams of high density polyethylene at a speed of 175–200 rpm for 30 seconds after flux. The fluxed pigmented resin is chopped up while warm and malleable, and then fed through a granulator. The resulting granules are molded on an injection molder with a 5 minute dwell time and a 30 second cycle time at a temperature of 260° C. Homogeneously colored chips which show a bright red color with excellent light stability are obtained.

EXAMPLE 10

1000 Grams of polypropylene granules (DAPLEN PT-55®, from Chemie Linz) and 10 grams of the pigment composition obtained in Example 1B are thoroughly mixed in a mixing drum. The granules so obtained are melt spun at 260°–285° C. to red filaments of good light fastness and textile fibers properties.

I claim:

1. A process for preparing a quinacridone of the formula I

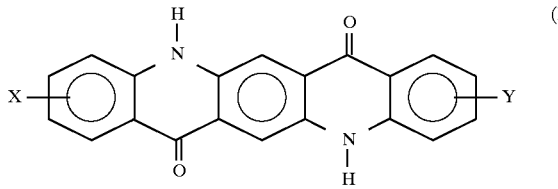

wherein X and Y are independently 1 or 2 substituents selected from the group consisting of H, F, Cl, $C_1$–$C_3$alkyl and $C_1$–$C_3$alkoxy, by the oxidation of a corresponding 6,13-dihydroquinacridone of the formula II

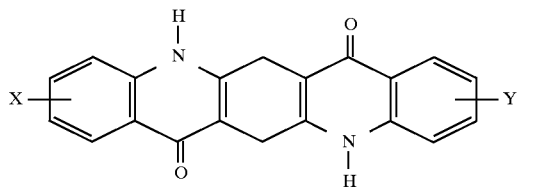

which comprises (a) premilling a 6,13-dihydroquinacridone of formula II to subpigmentary size;

(b) oxidizing the premilled 6,13-dihydroquinacridone to the corresponding quinacridone in a basic, aqueous reaction medium with hydrogen peroxide in the presence of a catalyst; and (c) isolating the quinacridone of formula I.

2. A process of claim 1, wherein the 6,13-dihydroquinacridone is premilled in an attritor.

3. A process of claim 1, wherein step (b) is carried out at a temperature of from 80° to 103° C.

4. A process of claim 1, wherein step (b) is carried out at a temperature of from 90° to 100° C.

5. A process of claim 1, wherein the basic, aqueous reaction medium comprises from 2 to 7 moles of an alkali metal hydroxide per mole of the 6,13-dihydroquinacridone.

6. A process of claim 5, wherein the basic, aqueous reaction medium comprises from 2.2 to 5 moles of the alkali metal hydroxide per mole of the 6,13-dihydroquinacridone.

7. A process of claim 5, wherein the alkali metal hydroxide is sodium or potassium hydroxide.

8. A process of claim 1, wherein the catalyst is selected from the group consisting of anthraquinone, anthraquinone monosulfonic acid and anthraquinone disulfonic acid, or a salt thereof.

9. A process of claim 8, wherein the catalyst is anthraquinone-2-sulfonic acid, sodium or potassium salt.

10. A process of claim 1, wherein the catalyst is present in an amount of from 0.005 to 0.1 times the weight of the 6,13-dihydroquinacridone.

11. A process of claim 1 wherein step (b) is carried out by combining a 1 to 50 percent by weight aqueous solution of hydrogen peroxide with a basic, aqueous slurry of the premilled 6,13-dihydroquinacridone.

12. A process of claim 11, wherein the aqueous hydrogen peroxide solution has a concentration of 5 to 30 weight percent of hydrogen peroxide.

13. A process of claim 11, wherein 1.1 to 5 moles of the hydrogen peroxide are present per mole of 6,13-dihydroquinacridone.

14. A process of claim 1, wherein step (b) is carried out by combining an aqueous solution of hydrogen peroxide with the aqueous slurry of premilled 6,13-dihydroquinacridone over a time interval of from ½ to 9 hours and then stirring the aqueous, basic reaction medium at an elevated temperature for from ½ to 12 hours to complete the oxidation and promote pigment recrystallization.

15. A process of claim 14, wherein the basic, aqueous reaction medium is stirred at a temperature of from 90° to 100° C. for from ½ to 12 hours.

16. A process of claim 15 wherein the basic, aqueous reaction medium is stirred for from 1 to 6 hours.

17. A process of claim 1, wherein the basic aqueous reaction medium contains 0.1 to 6 percent by weight based on 6,13-dihydroquinacridone of an antifoam agent.

18. A process of claim 17, wherein the aqueous reaction medium contains 0.5 to 4 percent by weight based on 6,13-dihydroquinacridone of an antifoam agent.

19. A process of claim 17, wherein the antifoam agent is a polyalkylene glycol derivative, a $C_5$–$C_{12}$alkyl alcohol or an alkylenediol.

20. A process of claim 19, wherein the polyalkylene glycol derivative is cetyloxypoly(ethylenoxy)ethanol with an average molecular weight of around 620.

21. A process of claim 19, wherein said alkylenediol is 1,2-dodecanediol.

22. A process of claim 1, wherein the quinacridone pigment is quinacridone, 2,9-dichloroquinacridone, 2,9-difluoroquinacridone, 4,11-dichloroquinacridone, 2,9-dimethylqinacridone or 2,9-dimethoxyquinacridone.

23. A process of claim 1, wherein the quinacridone pigment is a quinacridone pigment solid solution.

24. A process of claim 1, wherein the quinacridone pigment is a quinacridone/2,9-dichloroquinacridone, quinacridone/2,9-dimethylquinacridone, quinacridone/quinacridonequinone, 2,9-dichloroquinacridone/2,9-dimethylquinacridone or 2,9-dichloroquinacridone/2,9-dimethoxyqinacridone solid solution.

25. A process of claim 1, wherein the quinacridone pigment is the alpha, beta or gamma form of unsubstituted quinacridone.

26. A process of claim 25, wherein the quinacridone pigment is gamma-II quinacridone.

27. A process of claim 26, wherein the gamma-II quinacridone is polymorphically homogeneous.

28. A process of claim 26, wherein the gamma-II quinacridone is a pigment solid solution consisting essentially of from 85 to 99.8 percent by weight of quinacridone and 0.2 to 15 percent by weight of 6,13-dihydroquinacridone.

29. A process of claim 28, wherein the pigment solid solution consists essentially of 90 to 99.5 percent by weight of quinacridone and 0.5 to 10% by weight of 6,13-dihydroquinacridone.

30. A process of claim 28, wherein the pigment solid solution consists essentially of 92 to 99 percent by weight of quinacridone and 1 to 8 percent by weight of 6,13-dihydroquinacridone.

31. A process of claim 28, wherein the pigment solid solution has an x-ray diffraction pattern characterized by strong lines 6.6±0.2, 13.9±0.2 and 26.3±0.2; medium lines at 13.3±0.2, 23.6±0.2, 25.2±0.2 and 28.3±0.2; and weak lines at 17.1±0.2 and 20.4±0.2° 2θ double glancing angles.

* * * * *